(12) United States Patent
Maj et al.

(10) Patent No.: US 12,410,125 B2
(45) Date of Patent: Sep. 9, 2025

(54) METHOD FOR PURIFYING ALKYL HYDROPEROXIDE BY EXTRACTION WITH WATER AND SEPARATION OF THE AQUEOUS PHASE

(71) Applicant: ARKEMA FRANCE, Colombes (FR)

(72) Inventors: Philippe Maj, Pierre-Benite (FR); Albert Blum, Pierre-Benite (FR); Serge Hub, Pierre-Benite (FR); Bruno Van Hemelryck, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 1052 days.

(21) Appl. No.: 17/417,427

(22) PCT Filed: Dec. 20, 2019

(86) PCT No.: PCT/FR2019/053258
§ 371 (c)(1),
(2) Date: Jun. 23, 2021

(87) PCT Pub. No.: WO2020/136336
PCT Pub. Date: Jul. 2, 2020

(65) Prior Publication Data
US 2022/0073457 A1 Mar. 10, 2022

(30) Foreign Application Priority Data
Dec. 26, 2018 (FR) ...................... 1874173

(51) Int. Cl.
*C07C 407/00* (2006.01)
*B01D 3/14* (2006.01)
(Continued)

(52) U.S. Cl.
CPC .......... *C07C 407/003* (2013.01); *B01D 3/143* (2013.01); *B01D 11/0492* (2013.01); *C08K 5/14* (2013.01)

(58) Field of Classification Search
None
See application file for complete search history.

(56) References Cited

U.S. PATENT DOCUMENTS 2,430,864 A    11/1947    Farkas et al.
4,002,687 A    1/1977     D'Aubigne et al.
(Continued)

FOREIGN PATENT DOCUMENTS

EP    0404417 A1    12/1990
EP    1679107 A1    7/2006
(Continued)

OTHER PUBLICATIONS

Rusli, Arjulizan et al., Allylic monomers as reactive plasticizers of polyphenylene oxide. Part II: Cure kinetics, European Polymer Journal, Jul. 2, 2011, pp. 1785-1794, vol. 47, No. 9.
(Continued)

*Primary Examiner* — Joseph D Anthony
(74) *Attorney, Agent, or Firm* — NK Patent Law

(57) ABSTRACT

The present invention relates to a method for purifying a mixture containing at least one alkyl hydroperoxide, preferably tert-butyl hydroperoxide or tert-amyl hydroperoxide, and at least one corresponding dialkyl hydroperoxide, said method comprising at least one step of extraction with water and at least one separation step which is carried out within the aqueous phase, obtained following the extraction step, in order to recover an aqueous solution which is rich in alkyl hydroperoxide. The invention also relates to an aqueous composition which is rich in alkyl hydroperoxide and contains at least 0.1% by weight of dialkyl peroxide in relation to the total weight of the composition.

16 Claims, 1 Drawing Sheet

(51) Int. Cl.
    *B01D 11/04*     (2006.01)
    *C08K 5/14*     (2006.01)

(56) References Cited

U.S. PATENT DOCUMENTS

| | | |
|---|---|---|
| 4,381,222 A | 4/1983 | Brossmann et al. |
| 12,227,470 B2 * | 2/2025 | Van Hemelryck ....... B01D 3/40 |
| 2022/0073456 A1 * | 3/2022 | Van Hemelryck ....... B01D 3/40 |

FOREIGN PATENT DOCUMENTS

| | | |
|---|---|---|
| FR | 2203872 | 5/1974 |
| FR | 2455036 | 11/1980 |
| GB | 1137717 | 12/1968 |
| WO | 2004037782 A1 | 5/2004 |

OTHER PUBLICATIONS

Schmidt, Daniel, et al., Poly[N-(oxo-2-vinylanthracen-9(10H)-ylidene)cyanamide] as a Novel Cathode Material for Li-Organic Batteries, Journal of Polymer Science, Part A: Polymer Chemistry, Nov. 1, 2015, pp. 2517-2523, vol. 53.

PCT, International Search Report in International application No. PCT/FR2019-053258 dated Apr. 22, 2020.

\* cited by examiner

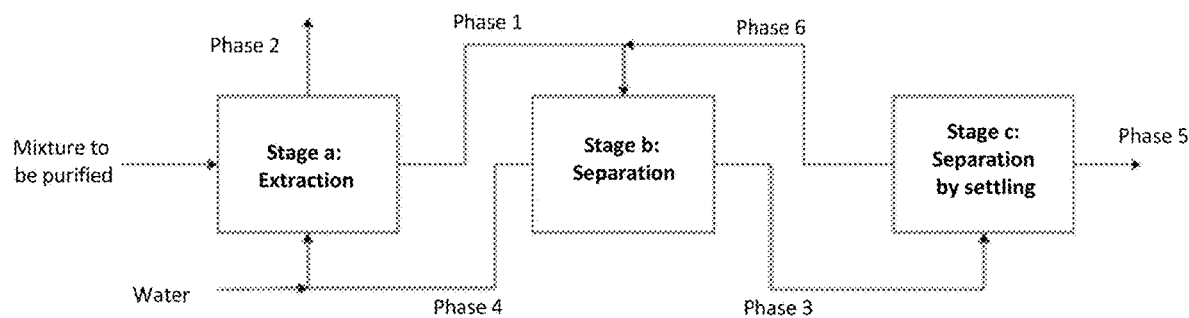

METHOD FOR PURIFYING ALKYL HYDROPEROXIDE BY EXTRACTION WITH WATER AND SEPARATION OF THE AQUEOUS PHASE

CROSS-REFERENCE TO RELATED APPLICATIONS

This application is a U.S. National Stage application of International Patent Application No. PCT/FR2019/053258, filed on Dec. 20, 2019, which claims the benefit of French Patent Application No. 1874173, filed on Dec. 26, 2018.

The present invention relates to a process for the purification of a mixture containing at least one alkyl hydroperoxide, preferably tert-butyl hydroperoxide or tert-amyl hydroperoxide, and at least one dialkyl peroxide, comprising at least one stage of extraction with water and at least one separation stage carried out on the aqueous phase obtained following the extraction stage, in order to recover an aqueous solution rich in alkyl hydroperoxide.

The invention also relates to an aqueous composition rich in alkyl hydroperoxide containing less than 0.1% by weight of dialkyl peroxide, with respect to the total weight of the composition.

Alkyl hydroperoxides are commonly used as raw materials to produce crosslinking agents, intended to be mixed with polymers, such as polyesters, copolymers of ethylene and of vinyl acetate (EVA) and ethylene/propylene/diene monomer terpolymers (EPDM), or radical polymerization initiators, such as peroxyesters or peresters, peroxyacetals or peracetals, as well as monoperoxypercarbonates or percarbonates, involved in the preparation of polymers, such as polystyrene or polyethylene.

The alkyl hydroperoxides available on the market generally contain impurities, mainly consisting of alkyl peroxides, in particular dialkyl peroxides, which originate from the preparation of the alkyl hydroperoxides in question. This is because alkyl hydroperoxides, in particular tert-alkyl hydroperoxides, are conventionally obtained by acid catalysis, leading to the formation of the associated dialkyl peroxides, which are generally present at between 3% and 30% by weight, with respect to the total weight of the composition of alkyl hydroperoxides.

By way of example, the preparation of tert-butyl hydroperoxide can be carried out by reaction of tertiary butanol with hydrogen peroxide in the presence of sulfuric acid, which will have the effect of catalyzing the undesired formation of di(tert-butyl) peroxide.

Such dialkyl peroxides are not desired in combination with their respective alkyl hydroperoxides and prove to be the main source of harmful contamination in the synthesis of crosslinking agents and of polymerization initiators.

More specifically, these impurities obtained in the alkyl hydroperoxide starting materials enter the process for the production of crosslinking agents for polymers and of polymerization initiators. This has the direct consequence of lowering the degree of purity of the products obtained. For certain applications, such as low-density polyethylene (LDPE) obtained by radical reaction of ethylene under very high pressure starting from a peroxide initiation, the presence of dialkyl peroxide in the initiators can be a source of poor thermal reaction profiles, harming the execution of the polymerization.

Research has thus been carried out with the aim of purifying the crosslinking agents and the polymerization initiators, in other words in order to remove these impurities, more particularly in this case in order to reduce the presence of dialkyl peroxides.

However, the results observed are not satisfactory at present; in particular, the purification yields are low and the physicochemical properties of the organic peroxides treated are partially degraded, which makes it difficult to obtain final products (crosslinked polymers or synthesized polymers) having good quality starting from these organic peroxides.

This is because, in the context of the preparation of the abovementioned tert-butyl hydroperoxide, the purification can be carried out by adding potassium hydroxide (KOH) or sodium hydroxide (NaOH) so as to form a water-soluble tert-butyl hydroperoxide salt. Thus, the salt and the di(tert-butyl) peroxide are easily separated by settling.

However, this purification stage often results in a significant dilution of the tert-butyl hydroperoxide, which decreases its effectiveness and further complicates its storage from an operational point of view as well as its transportation to the production units.

More generally, the formation of a water-soluble alkyl hydroperoxide salt in order to obtain separation from the corresponding dialkyl peroxide can result in numerous disadvantages on the industrial scale. This is because, when the use of the alkyl hydroperoxide and not that of its salt is required in the subsequent synthesis of a polymerization initiator or of a crosslinking agent, such as, for example, in the case of peroxyacetals, such as 1,1-di(tert-amylperoxy)cyclohexane, 1,1-di(tert-butylperoxy)-3,3,5-trimethylcyclohexane, 2,2-di(tert-butylperoxy)butane, 2,2-di(tert-amylperoxy)butane, ethyl 3,3-di(tert-amylperoxy)butyrate, ethyl 3,3-di(tert-butylperoxy)butyrate, n-butyl 4,4-di(tert-butylperoxy)valerate, and the like, the alkyl hydroperoxide salt is acidified in particular using an aqueous solution of sulfuric acid, in order to reform the alkyl hydroperoxide. The alkyl hydroperoxide is thus recovered by phase separation or by extraction with a solvent, for example a hydrocarbon. The major drawbacks of this technique originate, on the one hand, from its low productivity, if it is considered that the same reactor carries out the various stages (salt formation/separation by settling, reacidification/extraction), and, on the other hand, from the formation of large amounts of saline aqueous effluents. The aqueous effluents formed during the acidification, such as, for example, potassium sulfate, must be treated. In addition, the use of base and of acid increases the production costs.

Furthermore, the addition of a base at the time of the use of a mixture containing the alkyl hydroperoxide and the dialkyl peroxide can induce side reactions with the crosslinking agents and/or the polymerization initiators. For example, the use of potassium hydroxide (KOH) or of sodium hydroxide (NaOH) at the same time as the mixture based on alkyl hydroperoxide and on dialkyl peroxide can in particular result in the saponification of peroxyesters.

Consequently, the abovementioned disadvantages run counter to a rationalization of the costs of a process for the preparation of crosslinking agents or polymerization initiators on the industrial scale and also pose environmental problems, linked to the treatment of the saline aqueous effluents, as well as problems in terms of storage, transportation and effectiveness of the alkyl hydroperoxides.

In order to overcome these drawbacks, it has been envisaged in the prior art to implement a process making it possible to eliminate these impurities, more particularly the dialkyl peroxides, or at the very least to separate them from the starting materials, that is to say from the alkyl hydroperoxides, while trying to preserve the physicochemical properties of the latter.

To this end, the document FR 2 455 036 describes a process for the direct purification of alkyl hydroperoxides, in particular tert-amyl hydroperoxide (TAHP). In particular, the distillation of TAHP containing di(tert-amyl) peroxide (DTA) is carried out in the presence of water under reduced pressure and at a temperature of less than 45° C., making it possible to recover the TAHP at the column bottom. The distillation makes it possible to obtain a TAHP composition with a DTA residue of 0.8% (8000 ppm).

These results remain insufficient, in particular for the use of TAHP as starting materials for the production of polymerization initiators. In addition, the TAHP loss is significant, between 4% and 16%, due to a lack of selectivity during the separation of the DTA and/or to a thermal degradation of the TAHP.

Furthermore, purification methods consisting in using azeotropic compositions to separate the dialkyl peroxide from the alkyl hydroperoxide have already been described in the state of the art.

However, the various methods employed in the prior art do not yet make it possible, starting from a mixture of alkyl hydroperoxides and of dialkyl peroxides, to obtain an aqueous composition rich in alkyl hydroperoxides in which the amounts of dialkyl peroxides are sufficiently minimized to make possible efficient rationalization of the costs of preparation of crosslinking agents or of polymerization initiators while hindering their preparation as little as possible.

More specifically, the proposed and existing current solutions for purifying alkyl hydroperoxides of their associated peroxides are insufficient, which is in particular due to a lack of selectivity of the purification treatments, low yields obtained, production costs, but also to the safety conditions to be taken into account during the purification.

This is because it is important to note that the chemical nature of organic peroxides is to decompose thermally, with in particular the formation of flammable vapors.

For reasons of safety and of quality of the product to be purified, it is thus important to limit the treatment temperature as much as possible, which makes the purification of the alkyl hydroperoxides all the more difficult.

There is thus a real need to implement a process for the purification of a mixture based on at least one alkyl hydroperoxide and on at least one corresponding dialkyl peroxide capable of effectively resulting in an aqueous composition rich in alkyl hydroperoxide in which the amounts of impurities, such as alkyl peroxides, are minimized.

In other words, one of the objectives of the present invention is to provide a process which makes it possible to effectively separate an alkyl hydroperoxide from the corresponding dialkyl peroxide, in complete safety, in order to reduce the costs associated with the preparation of crosslinking agents and/or of polymerization initiators obtained from said alkyl hydroxyperoxide.

At the same time, one of the aims of the present invention is to purify alkyl hydroperoxides, starting from mixtures containing dialkyl peroxides, without degrading their physicochemical properties so as to be able to prepare crosslinking agents and/or polymerization initiators of good quality.

A subject matter of the present invention is thus in particular a process for the purification of a mixture containing at least one alkyl hydroperoxide, as defined below, and at least one dialkyl peroxide, said mixture being preferably obtained following the preparation of the alkyl hydroperoxide in question, comprising successively:

a) at least one stage of extraction, carried out with water, of the mixture so as to obtain a first phase rich in alkyl hydroperoxide and a second phase rich in dialkyl peroxide, and b) at least one stage of concentration of the content of alkyl hydroperoxide in the first phase obtained in stage a) so as to obtain two new phases, known as third and fourth phases, c) optionally a stage of separation by settling of the third phase so as to obtain a fifth and sixth phase, d) optionally a stage of recovery of the fifth phase obtained in stage c).

The process according to the invention makes it possible to recover a solution containing at least 60% by weight of alkyl hydroperoxide and less than 0.1% by weight of dialkyl peroxide, the proportions being calculated with respect to the total weight of the solution. The process according to the invention is thus a process for the separation of an alkyl hydroperoxide from a dialkyl peroxide.

In other words, stage a) consists of at least one stage of extraction, carried out with water, of the mixture.

In other words, stage b) consists of at least one stage of concentration of the content of alkyl hydroperoxide in the first phase (rich in alkyl hydroperoxide) obtained in stage a).

Thus, the invention relates to a process for the purification of a mixture containing at least one alkyl hydroperoxide, as defined below, and at least one dialkyl peroxide, said mixture being preferably obtained following the preparation of the alkyl hydroperoxide in question, comprising successively:

a) at least one stage of extraction, carried out with water, of the mixture, and b) at least one stage of concentration of the content of alkyl hydroperoxide in the first phase rich in alkyl hydroperoxide obtained in stage a), c) optionally a stage of separation by settling of the third phase rich in alkyl hydroperoxide obtained in stage b), d) optionally a stage of recovery of the fifth phase rich in alkyl hydroperoxide obtained in stage c).

The extraction stage a) makes it possible to entrain the alkyl hydroperoxide in a first phase, while the dialkyl peroxide as well as the possible byproducts, resulting from the method for the preparation of the alkyl hydroperoxide, remain in the second phase.

Thus, there advantageously results, from stage a), the appearance of two phases:

a first lower phase (rich in alkyl hydroperoxide);

a second upper phase (rich in dialkyl peroxide).

The concentration stage b) is targeted in particular at carrying out a stage of separation, of the first phase obtained in stage a), into two new phases:

a third phase rich in alkyl hydroperoxide and a fourth aqueous phase depleted in alkyl hydroperoxide.

In other words, stage b) consists of at least one stage of concentration of the content of alkyl hydroperoxide in the first phase obtained in stage a).

Thus, there advantageously results, from stage b), the appearance of two phases starting from the first phase obtained in stage a):

a third upper phase (rich in alkyl hydroperoxide);

a fourth lower phase (poor in alkyl hydroperoxide).

The third phase spontaneously separates by settling into two new phases:

a fifth upper phase (rich in alkyl hydroperoxide);

a sixth lower phase (poor in alkyl hydroperoxide).

The concentration stage b) consists in concentrating the content of the alkyl hydroperoxide in the first phase, extracted in stage a), in order to obtain a fifth phase containing at least 60% by weight of alkyl hydroperoxide and less than 0.1% by weight of dialkyl peroxide.

In other words, the process according to the invention is a process for the separation of an alkyl hydroperoxide, as defined below, and of a dialkyl peroxide comprising:

a) at least one stage of extraction, with water, of a mixture containing the two compounds mentioned, in particular obtained following the preparation of an alkyl hydroperoxide, in order to result in the formation of two phases, b) at least one stage of separation of the lower phase obtained in stage a) so as to obtain two new phases, known as third and fourth phases, c) optionally a stage of separation by settling of the third phase so as to obtain a fifth and sixth phase, d) optionally a stage of recovery of the fifth phase obtained in stage c).

The fifth phase is the upper phase obtained in stage c), which is rich in alkyl hydroperoxide.

The process according to the invention thus makes it possible to result in an aqueous composition rich in alkyl hydroperoxide in which the amounts of impurities, such as dialkyl peroxides, are minimized.

Thus the process according to the invention results in a selective removal of the dialkyl peroxide from the corresponding alkyl hydroperoxide with a reduced loss of alkyl hydroperoxide.

In this way, the process according to the invention makes it possible to prepare an alkyl hydroperoxide of good quality, that is to say without its physicochemical properties being degraded, so as to be able to efficiently prepare crosslinking agents and/or polymerization initiators.

In particular, the process according to the invention makes it possible to reduce the amounts of dialkyl peroxides in an aqueous solution rich in alkyl hydroperoxide and, consequently, to minimize the risks of hindering the preparation of crosslinking agents and/or polymerization initiators obtained from the alkyl hydroperoxide.

More particularly, the risks of initiation of side reactions generated by the presence of dialkyl peroxides during the preparation of crosslinking agents and/or of polymerization initiators can be advantageously avoided.

The process according to the invention also exhibits the advantage of rationalizing the costs of preparation of crosslinking agents and/or polymerization initiators and of reducing the environmental risks.

In addition, the process according to the invention makes it possible, by removing the dialkyl peroxide, to reduce the safety problems associated with the storage and/or transportation of an aqueous composition based on alkyl hydroperoxide.

In addition, the process makes it easy to recycle the water which has contributed to the purification.

The process according to the invention can be carried out batchwise or continuously.

The invention also relates to an aqueous composition containing at least 60% by weight of alkyl hydroperoxide and less than 0.1% by weight of dialkyl peroxide, the proportions being calculated by weight with respect to the total weight of the composition.

The aqueous composition obtained with the process according to the invention exhibits the advantage of having available a small amount of impurities which ensures efficiently preparing crosslinking agents and/or polymerization initiators.

The present invention also relates to the use of the composition as defined above for the preparation of crosslinking agents or of polymerization initiators, preferably chosen from the group consisting of organic peroxides, in particular peroxyesters and peroxyacetals.

Other characteristics and advantages of the invention will become more clearly apparent on reading the description and the examples which follow.

In that which will follow, and unless otherwise indicated, the limits of a range of values are included in this document.

The expression "at least one" is equivalent to the expression "one or more".

BRIEF DESCRIPTION OF THE FIGURE

FIG. 1 diagrammatically presents the process according to the invention.

DESCRIPTION OF EMBODIMENTS OF THE INVENTION

Process
Preparation of a Hydroperoxide

As indicated above, the process according to the invention relates to the purification of a mixture comprising at least one alkyl hydroperoxide and at least one dialkyl peroxide.

Preferably, said mixture is obtained following the preparation of the alkyl hydroperoxide in question.

In other words, the process according to the invention is targeted at purifying an alkyl hydroperoxide obtained by synthesis.

Preferably, the alkyl hydroperoxide can be prepared in an acidic medium.

In other words, the process according to the invention can comprise a stage a'), prior to stage a), of synthesis of said alkyl hydroperoxide in an acidic medium.

In this case, the method of preparation of the alkyl hydroperoxide consists in particular in reacting aqueous hydrogen peroxide solution in the presence of at least one alcohol or of at least one alkene in an acidic medium.

Preferably, the method of preparation of the alkyl hydroperoxide consists in particular in reacting aqueous hydrogen peroxide solution in the presence of at least one alcohol or one unsaturated compound in an acidic medium.

The reaction can be carried out at a temperature which can range from 10° C. to 80° C., preferably 20° C. to 40° C.

Preferably, the reaction is carried out in the presence of one or more inorganic or organic acids, in particular one or more inorganic acids.

More preferentially, the inorganic acid is sulfuric acid.

The mixture can thus comprise at least one alkyl hydroperoxide, at least one corresponding dialkyl peroxide and at least one alcohol.

Preferably, said at least one dialkyl peroxide is a dialkyl peroxide corresponding to the alkyl hydroperoxide to be purified.

The term "corresponding dialkyl peroxide" is understood to mean, within the meaning of the present invention, the alkyl peroxide which originates from the synthesis of the alkyl hydroperoxide.

In other words, the corresponding dialkyl peroxide refers to the compound which is formed during synthesis of the alkyl hydroperoxide.

The mixture can comprise at least one alkyl hydroperoxide in a content of at least 40% by weight, preferably 50% by weight, preferably 60% by weight and more preferentially 68%, with respect to the total weight of the mixture.

The mixture can comprise at least 1% by weight, preferably at least 2% by weight, more preferentially at least 3% by weight, of dialkyl peroxide, with respect to the total weight of the mixture.

Preferably, the mixture can comprise less than 25%, preferably less than 10% by weight, preferably less than 8% by weight, of dialkyl peroxide, with respect to the total weight of the mixture.

The alkyl hydroperoxide can also be obtained by oxidation of at least one alkane or of at least one corresponding alkene.

The mixture can thus comprise at least one alkyl hydroperoxide, at least one corresponding dialkyl peroxide, at least one alkane or at least one alkene in the presence of one or more oxidizing agents.

Stage a) of Extraction with Water

The process according to the invention comprises at least one stage a) of extraction, carried out with water, of the mixture as defined above.

Stage a) of extraction with water can be carried out one or more times according to the conventional liquid extraction processes as described, for example, in the work entitled "Chemical Engineer's Handbook", $5^{th}$ edition of 1973, Perry et al.

Preferably, the extraction stage a) is carried out by bringing water into contact with the mixture, as defined above, preferably obtained following the preparation of the alkyl hydroperoxide.

Preferably, the extraction stage a) is carried out with an excess amount of water, with respect to the total weight of the mixture as defined above.

More preferentially, the extraction stage a) is carried out with a water content which is 5 times greater, in particular 10 times greater, more particularly 15 times greater, than the content by weight of the mixture defined above.

Advantageously, the extraction stage a) is carried out with a water content which is 10 times greater than the content by weight of the mixture defined above.

The extraction stage a) is carried out so as to obtain two phases.

Thus, the extraction stage a) is carried out so as to obtain:
a first phase (rich in alkyl hydroperoxide);
a second phase (rich in dialkyl peroxide).

The first phase contains the alkyl hydroperoxide and a fraction by weight of the corresponding dialkyl peroxide. In particular, the alkyl hydroperoxide is water-soluble.

The term "rich in alkyl hydroperoxide" is understood to mean that this phase contains more than 70%, preferably more than 80%, more preferably more than 90% by weight of the hydroperoxide present in the mixture before stage a).

The term "water-soluble" is understood to mean, within the meaning of the present invention, that the alkyl hydroperoxide exhibits, at a temperature of 25° C. and at atmospheric pressure (760 mm Hg, i.e. $1.013 \times 10^5$ Pa), a solubility in water of at least 4% by weight.

The second phase contains a predominant fraction by weight of the dialkyl peroxide, in particular the complementary predominant fraction by weight of the dialkyl peroxide occurring in the first phase.

The second phase can also contain, for example, at least alcohol and optionally one or more byproducts, resulting from the method for the preparation of the alkyl hydroperoxide, which are soluble in the second phase.

The formation of two phases, after the extraction stage a), takes place in particular at the time of the separation by settling of the composition resulting from the mixture, as defined above, and of the water.

Once separated by settling, the second phase is located above the first phase.

Stage a) can be carried out batchwise or continuously.

Concentration Stage b)

The first phase is recovered following stage a) of extraction with water.

The concentration stage b) consists in particular in separating, from the first phase obtained in stage a), a third phase rich in alkyl hydroperoxide and a fourth phase depleted in alkyl hydroperoxide.

Stage b) can be carried out starting from a process employing at least one semi-permeable membrane or from a distillation process.

The term "semi-permeable membrane" is understood to mean, within the meaning of the present invention, a selective organic or synthetic membrane capable of allowing a large amount of water to pass through and not the substances occurring in solution.

In this way, a process employing at least one semi-permeable membrane makes it possible to recover a solution rich in water, i.e. an aqueous phase depleted in alkyl hydroperoxide, and an aqueous solution enriched in alkyl hydroperoxide.

The process employing at least one semi-permeable membrane can be a reverse osmosis process or a pervaporation process.

Preferably, stage b) is carried out starting from a distillation process.

This is because the distillation process exhibits the advantage of leading to efficient and rapid separation.

Preferably, the distillation is carried out at a temperature of between 25° C. and 60° C., preferentially between 30° C. and 45° C.

Advantageously, the distillation is carried out at a pressure of between 5 and 300 mbar (millibars), preferentially between 30 and 200 mbar, preferentially between 40 and 180 mbar and more preferentially between 50 and 160 mbar.

The fourth phase depleted in alkyl hydroperoxide is preferably a solution containing less than 6%, preferably less than 5%, preferably less than 4%, preferably less than 3%, preferably less than 2%, preferably less than 1%, by weight of alkyl hydroperoxide, with respect to the total weight of the solution.

The fourth phase depleted in alkyl hydroperoxide is advantageously recycled to the extraction stage a) so as to retain the amount of water necessary to carry out stage a).

The recycling can be carried out continuously or noncontinuously.

Stage c) of Separation by Settling

The third phase obtained in stage b) spontaneously separates by settling into two new phases:
a fifth upper phase (rich in alkyl hydroperoxide);
a sixth lower phase (poor in alkyl hydroperoxide).

The fifth phase rich in alkyl hydroperoxide is a solution containing at least 60% by weight of alkyl hydroperoxide and less than 0.1% by weight of dialkyl peroxide.

At the end of stage c), a fifth phase containing at least 60% by weight of alkyl hydroperoxide and less than 0.1% by weight of dialkyl peroxide, the proportions being calculated by weight with respect to the total weight of the solution, is recovered.

Preferably, the fifth phase contains at least 60% by weight, preferably at least 68% by weight, of alkyl hydroperoxide, with respect to the total weight of the solution.

Stage c) makes it possible to separate the solution containing at least 60% by weight of alkyl hydroperoxide and less than 0.1% by weight of dialkyl peroxide and a solution containing less than 20% by weight of alkyl hydroperoxide, preferably less than 15%, the proportions being calculated with respect to the total weight of the solution.

Alky Hydroperoxide and Dialkyl Peroxide

As indicated above, the process according to the invention relates to the purification of a mixture comprising at least one alkyl hydroperoxide and at least one dialkyl peroxide.

The alkyl hydroperoxide preferably corresponds to the following general formula $R^1$—OO—H in which $R^1$ represents:
- a linear or branched $C_4$-$C_{10}$, preferably $C_4$-$C_8$, more preferentially $C_4$-$C_6$, alkyl group optionally substituted by one or more hydroxyl groups or
- a cyclic group comprising from 5 to 8 carbon atoms which is optionally aromatic and which is optionally substituted by one or more $C_1$-$C_3$ alkyl groups.

In particular, $R^1$ can represent a cyclic group comprising from 5 to 8 carbon atoms which is optionally aromatic and which is optionally substituted by one or more $C_1$-$C_3$ alkyl groups, in particular by a $C_1$ alkyl group.

More particularly, $R^1$ can represent a nonaromatic cyclic group comprising from 5 to 8 carbon atoms which is optionally substituted by a $C_1$ alkyl group.

Preferably, the alkyl hydroperoxide is a tert-alkyl hydroperoxide.

Preferably, $R^1$ represents a branched $C_4$-$C_{10}$, preferably $C_4$-$C_8$, more preferentially $C_4$-$C_6$, more preferentially still $C_4$-$C_8$, alkyl group.

Preferably, the alkyl hydroperoxide is chosen from the group consisting of tert-butyl hydroperoxide, tert-amyl hydroperoxide, hexylene glycol hydroperoxide, tert-octyl hydroperoxide, tert-hexyl hydroperoxide, methylcyclopentyl hydroperoxide and methylcyclohexyl hydroperoxide.

More preferentially, the alkyl hydroperoxide is chosen from the group consisting of tert-butyl hydroperoxide (TBHP) and tert-amyl hydroperoxide (TAHP), more preferentially still tert-amyl hydroperoxide (TAHP).

Advantageously, the dialkyl peroxide corresponds to the following general formula $R^2$—OO—$R^3$ in which $R^2$ and $R^3$, which are identical or different, in particular identical, represent:
- a linear or branched $C_4$-$C_{10}$, preferably $C_4$-$C_8$, more preferentially $C_4$-$C_6$, alkyl group optionally substituted by one or more hydroxyl groups, or
- a cyclic group comprising from 5 to 8 carbon atoms which is optionally aromatic and which is optionally substituted by one or more $C_1$-$C_3$, in particular $C_1$, alkyl groups.

In particular, $R^2$ and $R^3$ can represent a cyclic group comprising from 5 to 8 carbon atoms which is optionally aromatic and which is optionally substituted by one or more $C_1$-$C_3$, in particular $C_1$, alkyl groups.

More particularly, $R^1$ and $R^3$ can represent a nonaromatic cyclic group comprising from 5 to 8 carbon atoms which is optionally substituted by a $C_1$ alkyl group.

Preferably, the dialkyl peroxide is a di(tert-alkyl) peroxide.

Preferably, $R^2$ and $R^3$, which are identical or different, represent a branched $C_4$-$C_{10}$, preferably $C_4$-$C_8$, more preferentially $C_4$-$C_6$, alkyl group optionally substituted by one or more hydroxyl groups.

Preferably, $R^2$ and $R^3$, which are identical or different, represent a branched $C_4$-$C_{10}$, preferably $C_4$-$C_8$, more preferentially $C_4$-$C_6$, alkyl group.

More preferentially still, the dialkyl peroxide is symmetrical, that is to say that the groups flanking the O—O group are identical. In other words, $R^2$ and $R^3$ are more preferentially identical and represent a branched $C_4$-$C_{10}$, preferably $C_4$-$C_8$, more preferentially $C_4$-$C_6$, alkyl group.

Preferably, the dialkyl peroxide is chosen from the group consisting of di(tert-butyl) peroxide, di(tert-amyl) peroxide, di(3-hydroxy-1,1-dimethylbutyl) peroxide, di(tert-octyl) peroxide, di(tert-hexyl) peroxide, di(methylcyclopentyl) peroxide and di(methylcyclohexyl) peroxide.

More preferentially, the dialkyl peroxide is chosen from the group consisting of di(tert-butyl) and di(tert-amyl) peroxide.

More preferentially still, the dialkyl peroxide is di(tert-amyl) peroxide.

Advantageously, the alkyl hydroperoxide and the dialkyl peroxide exhibit identical $R^1$, $R^2$ and $R^3$ groups.

Preferably, the alkyl hydroperoxide is tert-amyl hydroperoxide (TAHP) and the dialkyl peroxide is di(tert-amyl) peroxide (DTA).

Alternatively, the alkyl hydroperoxide is preferably tert-butyl hydroperoxide (TBHP) and the dialkyl peroxide is di(tert-butyl) peroxide (DTBP).

Alternatively, the alkyl hydroperoxide is hexylene glycol hydroperoxide and the dialkyl peroxide is di(3-hydroxy-1,1-dimethylbutyl) peroxide.

Alternatively, the alkyl hydroperoxide is tert-octyl hydroperoxide and the dialkyl peroxide is di(tert-octyl) peroxide.

Alternatively, the alkyl hydroperoxide is tert-hexyl hydroperoxide and the dialkyl peroxide is di(tert-hexyl) peroxide.

According to an advantageous embodiment, the invention relates to a process for the purification of a mixture containing at least one alkyl hydroperoxide chosen from the group consisting of tert-amyl hydroperoxide, tert-butyl hydroperoxide, hexylene glycol hydroperoxide, tert-octyl hydroperoxide and tert-hexyl hydroperoxide, and at least one dialkyl peroxide chosen from the group consisting of di(tert-amyl) peroxide, di(tert-butyl) peroxide, di(3-hydroxy-1,1-dimethylbutyl) peroxide, di(tert-octyl) peroxide and di(tert-hexyl) peroxide, said mixture preferably being obtained following the preparation of the alkyl hydroperoxide in question, comprising successively:
  a) at least one stage of extraction, carried out with water, of the mixture so as to obtain a first phase rich in alkyl hydroperoxide and a second phase rich in dialkyl peroxide,
  b) at least one stage of distillation of the first phase obtained in stage a),
  c) optionally a stage of separation by settling of the third phase so as to obtain a fifth and sixth phase,
  d) optionally a stage of recovery of the fifth phase obtained in stage c).

In accordance with this embodiment, the mixture is obtained in particular following the preparation of the alkyl hydroperoxide in an acidic medium.

Composition

The invention also relates to an aqueous composition containing at least 60% by weight of alkyl hydroperoxide as defined above and less than 0.1% by weight of dialkyl peroxide as defined above, the proportions being calculated by weight with respect to the total weight of the composition.

Preferably, the aqueous composition contains at least 68% by weight of alkyl hydroperoxide as defined above, more preferentially at least 80% by weight.

Preferably, $R^1$ represents a branched, optionally substituted, $C_4$-$C_{10}$, preferably $C_5$-$C_{10}$, preferably $C_5$-$C_8$, more preferentially $C_5$-$C_6$, more preferentially still $C_5$, alkyl group.

The alkyl hydroperoxide is preferably chosen from the group consisting of tert-amyl hydroperoxide, hexylene glycol hydroperoxide, tert-octyl hydroperoxide and tert-hexyl hydroperoxide.

More preferentially, the alkyl hydroperoxide is tert-amyl hydroperoxide (TAHP).

Advantageously, the aqueous composition contains less than 0.08% by weight, preferably less than 0.07% by weight, of dialkyl peroxide, preferably less than 0.05% by weight of dialkyl peroxide, preferably less than 0.025% by weight of dialkyl peroxide, more preferentially less than 0.01% by weight of dialkyl peroxide, with respect to the total weight of the composition.

Preferably, the dialkyl peroxide chosen from the group consisting of di(tert-amyl) peroxide, di(3-hydroxy-1,1-dimethylbutyl) peroxide, di(tert-octyl) peroxide and di(tert-hexyl) peroxide.

More preferentially, the dialkyl peroxide is di(tert-amyl) peroxide.

Advantageously, the aqueous composition contains at least 60% by weight of tert-amyl hydroperoxide (TAHP) and less than 0.1% by weight of di(tert-amyl) peroxide (DTA), the proportions being calculated by weight with respect to the total weight of the composition.

The present invention also relates to an aqueous composition rich in alkyl hydroperoxide capable of being obtained by the process according to the invention.

Use of the Composition

The present invention also relates to the use of the composition as defined above for the preparation of crosslinking agent(s) or polymerization initiator(s).

Preferably, the initiator(s) is or are initiators of polymerization by the radical route, in particular of ethylene under high pressure.

The term "high pressure" is understood to mean, within the meaning of the present invention, a pressure of greater than 50 MPa. Preferably, the pressure varies from 500 bar (50 MPa) to 3000 bar (300 MPa), preferentially from 1200 bar (120 MPa) to 3000 bar (300 MPa), better still from 1200 bar (120 MPa) to 2600 bar (260 MPa).

Preferably, the crosslinking agents or the polymerization initiators are chosen from the group consisting of organic peroxides, in particular peroxyesters, hemiperoxyacetals and peroxyacetals.

The term "hemiperoxyacetal" is understood to mean a compound of general formula $(R_3)(R_4)C(-OR_1)(-OOR_2)$, in which:

$R_1$ represents a linear or branched, preferably $C_1$-$C_{12}$, preferably $C_1$-$C_4$, more preferably $C_1$, alkyl group or a cycloalkyl group with $R_2$, $R_2$ represents a linear or branched, preferably $C_1$-$C_{12}$, preferably $C_4$-$C_{12}$, more preferably $C_5$, alkyl group or a cycloalkyl group with $R_1$, $R_3$ represents a hydrogen or a linear or branched, preferably $C_1$-$C_{12}$, more preferably $C_4$-$C_{12}$, alkyl group or a cycloalkyl group with $R_4$, $R_4$ represents a hydrogen or a linear or branched, preferably $C_1$-$C_{12}$, more preferably $C_4$-$C_{12}$, alkyl group or a cycloalkyl group with $R_3$.

Preferably, $R_3$ forms a cycloalkyl group with $R_4$.

Preferably, when $R_3$ is a hydrogen, $R_4$ is a linear or branched, preferably $C_1$-$C_{12}$, more preferably $C_4$-$C_{12}$, alkyl group.

The following examples serve to illustrate the invention without limiting it.

EXAMPLES

Example 1

Starting Mixture

In the following example, the mixture treated is a solution of tert-amyl hydroperoxide (TAHP) containing 84.6% of tert-amyl hydroperoxide, 4% of di(tert-amyl) peroxide (DTA), 0.8% of acetone, 0.8% of tert-amyl alcohol and 0.9% by weight of the peroxide 2,2-di(tert-amylperoxy)propane.

Extraction Stage a)

In a closed flask, 500 ml of softened water are added to 41.2 g of the tert-amyl hydroperoxide solution described above.

The combined product is mixed for 30 minutes using a magnetic stirrer bar and is then left to separate by settling for a period of 30 minutes at ambient temperature.

Following this separation by settling, a supernatant organic phase (with the interface) of approximately 12.5 g and a slightly cloudy lower phase of approximately 528 g are formed.

Concentration Stage b)

The lower phase is introduced into a rotary evaporator flask.

The distillation takes place under 100 mbar of absolute pressure at a bath temperature of 50° C. A fifth of the aqueous phase is distilled off.

The distillate separates into an upper phase of 19 grams containing 89.2% of tert-amyl hydroperoxide (TAHP) and only 0.06% of di(tert-amyl) peroxide (DTA) and a lower phase containing 5.5% of tert-amyl hydroperoxide.

The distillation residue represents 405 g containing 0.35% of TAHP.

Example 2

Starting Mixture

In the following example, the mixture treated is a solution of tert-amyl hydroperoxide (TAHP) containing 84.6% of tert-amyl hydroperoxide, 4% of di(tert-amyl) peroxide (DTA), 0.8% of acetone, 0.8% of tert-amyl alcohol and 0.9% by weight of the peroxide 2,2-di(tert-amylperoxy)propane.

The starting mixture is identical to that of example 1.

Extraction Stage a)

In a closed flask, 500 ml of softened water are added to 41.2 g of the tert-amyl hydroperoxide solution described above.

The combined product is mixed for 30 minutes using a magnetic stirrer bar and is then left to separate by settling for a period of 60 hours at ambient temperature.

Following this separation by settling, a supernatant phase of approximately 11.5 g and a lower phase of approximately 526 g are formed.

Concentration Stage b)

A quantity of 428 g of lower phase is introduced into a rotary evaporator flask.

The distillation takes place under 100 mbar of absolute pressure at a bath temperature of 50° C. Half of the lower phase is distilled off.

The distillate separates into an upper phase of 11.5 grams containing 89% of tert-amyl hydroperoxide (TAHP) and only 0.005% of di(tert-amyl) peroxide (DTA) and a lower phase containing 4.7% of tert-amyl hydroperoxide.

The distillation residue represents 205 g containing 0.02% of TAHP.

The invention claimed is:

1. A process for the purification of a mixture containing at least one alkyl hydroperoxide and at least one dialkyl peroxide, wherein it successively comprises:
   a) at least one stage of extraction, carried out with water, of said mixture so as to obtain a first phase rich in alkyl hydroperoxide and a second phase rich in dialkyl peroxide, wherein the extraction stage a) is carried out with a water content which is at least 5 times greater than a content by weight of the mixture,
   b) at least one stage of concentration of the first phase obtained in stage a) so as to obtain two new phases, known as third and fourth phase,
   c) optionally a stage of separation by settling of the third phase so as to obtain a fifth and sixth phase,
   d) optionally a stage of recovery of the fifth phase obtained in stage c).

2. The process as claimed in claim 1, wherein the concentration stage b) is carried out starting from a process employing at least one semipermeable membrane or from a distillation process.

3. The process as claimed in claim 1, further comprising stage c), a stage of separation by settling of the third phase so as to obtain a fifth and sixth phase, wherein the concentration stage b) is carried out in order to obtain a fifth phase containing at least 60% by weight of alkyl hydroperoxide and less than 0.1% by weight of dialkyl peroxide and the fourth phase is a solution containing less than 6% by weight of alkyl hydroperoxide, the proportions being calculated with respect to the total weight of the solution as defined in claim 1.

4. The process as claimed in claim 3, wherein the solution containing less than 6% by weight of alkyl hydroperoxide is recycled to the extraction stage a).

5. The process as claimed in claim 1, wherein the concentration stage b) is a distillation carried out at a temperature of between 25° C. and 60° C.

6. The process as claimed in claim 1, wherein the concentration stage b) is a distillation carried out at a pressure of between 5 and 300 mbar (millibars).

7. The process as claimed in claim 1, wherein the alkyl hydroperoxide corresponds to the following general formula $R^1$—OO—H in which $R^1$ represents:
   a linear or branched $C_4$-$C_{10}$ alkyl group optionally substituted by one or more hydroxyl groups or
   a cyclic group comprising from 5 to 8 carbon atoms which is optionally aromatic and which is optionally substituted by one or more $C_1$-$C_3$ alkyl groups.

8. The process as claimed in claim 1, wherein $R^1$ represents a cyclic group comprising from 5 to 8 carbon atoms which is optionally aromatic or a branched $C_4$-$C_{10}$.

9. The process as claimed in claim 1, wherein the alkyl hydroperoxide is selected from the group consisting of tert-butyl hydroperoxide, tert-amyl hydroperoxide, hexylene glycol hydroperoxide, tert-octyl hydroperoxide, tert-hexyl hydroperoxide, methylcyclopentyl hydroperoxide and methylcyclohexyl hydroperoxide.

10. The process as claimed in claim 1, wherein the alkyl hydroperoxide is selected from the group consisting of tert-butyl hydroperoxide (TBHP) and tert-amyl hydroperoxide (TAHP).

11. The process as claimed in claim 1, wherein the dialkyl peroxide corresponds to the following general formula $R^2$—OO—$R^3$ in which $R^2$ and $R^3$, which are identical or different, represent:
   a linear or branched $C_4$-$C_{10}$ alkyl group optionally substituted by one or more hydroxyl groups, or
   a cyclic group comprising from 5 to 8 carbon atoms which is optionally aromatic and which is optionally substituted by one or more $C_1$-$C_3$ alkyl groups.

12. The process as claimed in claim 1, wherein $R^2$ and $R^3$, which are identical or different, represent a branched $C_4$-$C_{10}$ alkyl group optionally substituted by one or more hydroxyl groups.

13. The process as claimed in claim 1, wherein the dialkyl peroxide is selected from the group consisting of di(tert-butyl) peroxide, di(tert-amyl) peroxide, di(3-hydroxy-1,1-dimethylbutyl) peroxide, di(tert-octyl) peroxide, di(tert-hexyl) peroxide, di(methylcyclopentyl) peroxide and di(methylcyclohexyl) peroxide.

14. The process as claimed in claim 1, wherein the dialkyl peroxide is selected from the group consisting of di(tert-butyl) peroxide and di(tert-amyl) peroxide.

15. The process as claimed in claim 1, wherein the alkyl hydroperoxide and the dialkyl peroxide exhibit identical $R^1$, $R^2$ and $R^3$ groups.

16. The process as claimed in claim 1, in which the hydroperoxide is prepared in an acidic medium.

* * * * *